(12) United States Patent
Wolff

(10) Patent No.: US 12,201,535 B2
(45) Date of Patent: *Jan. 21, 2025

(54) SURGICAL ACCESS SYSTEM AND METHOD

(71) Applicant: Spineology Inc., St. Paul, MN (US)

(72) Inventor: Kyle Wolff, St. Paul Park, MN (US)

(73) Assignee: Spineology Inc., St. Paul, MN (US)

( * ) Notice: Subject to any disclaimer, the term of this patent is extended or adjusted under 35 U.S.C. 154(b) by 4 days.

This patent is subject to a terminal disclaimer.

(21) Appl. No.: 18/128,835

(22) Filed: Mar. 30, 2023

(65) Prior Publication Data

US 2023/0293313 A1    Sep. 21, 2023

Related U.S. Application Data

(63) Continuation of application No. 17/503,244, filed on Oct. 15, 2021, now Pat. No. 11,617,663.

(60) Provisional application No. 63/092,494, filed on Oct. 15, 2020.

(51) Int. Cl.
*A61F 2/46* (2006.01)
*A61F 2/44* (2006.01)

(52) U.S. Cl.
CPC .......... *A61F 2/4611* (2013.01); *A61F 2/4455* (2013.01); *A61F 2002/4625* (2013.01)

(58) Field of Classification Search
CPC ........ A61F 2/4611; A61F 2/4455; A61F 2/46; A61B 17/3417; A61B 17/3421; A61B 17/3423; A61B 17/02; A61B 2017/3445
USPC .................................. 600/201–246; 606/279
See application file for complete search history.

(56) References Cited

U.S. PATENT DOCUMENTS

| | | | |
|---|---|---|---|
| 11,617,663 B2 * | 4/2023 | Wolff | A61B 90/57 606/279 |
| 2015/0190128 A1 * | 7/2015 | Fenn | A61B 1/32 600/204 |
| 2020/0405503 A1 * | 12/2020 | Holladay | A61B 17/320016 |

* cited by examiner

*Primary Examiner* — Eduardo C Robert
*Assistant Examiner* — Christina Negrellirodriguez
(74) *Attorney, Agent, or Firm* — Skaar Ulbrich Macari, P.A.

(57) ABSTRACT

Disclosed are instruments, implants and methods of accessing the spine from an Anterior to the Psoas (ATP) approach, performing a discectomy through an ATP approach and then placing an intervertebral implant via an ATP approach for spinal fusion.

4 Claims, 6 Drawing Sheets

SURGICAL ACCESS SYSTEM AND METHOD

PRIORITY

This application is a continuation of U.S. patent application Ser. No. 17/503,244, filed Oct. 15, 2021, which claims the benefit of U.S. Provisional Application Ser. No. 63/092,494, filed on Oct. 15, 2020, and both of which are hereby incorporated herein by reference in their entirety.

FIELD

The present invention generally relates to surgical instruments and a method of accessing and treating the spine. More particularly, the present invention relates to instruments and methods for accessing the spine from an Anterior to the Psoas ("ATP") approach.

BACKGROUND

It is desirable to access surgical sites to minimize disruption to surrounding anatomy, particularly delicate vasculature. To that end, accessing the spine from an ATP approach can be beneficial in protecting the patient's vasculature. An ATP approach, that is, in front of the psoas muscle reduces the risk of contacting the ventral vessels, specifically the vena cava.

SUMMARY

The present invention is directed toward instruments, implants, systems and methods of accessing the spine from an ATP approach, performing a discectomy through a ATP approach and then placing an intervertebral implant via an ATP approach for spinal fusion.

The detailed technology and preferred embodiments implemented for the subject invention are described in the following paragraphs accompanying the appended drawings for people skilled in this field to well appreciate the features of the claimed invention. It is understood that the features mentioned hereinbefore and those to be commented on hereinafter may be used not only in the specified combinations, but also in other combinations or in isolation, without departing from the scope of the present invention.

Figure 1:
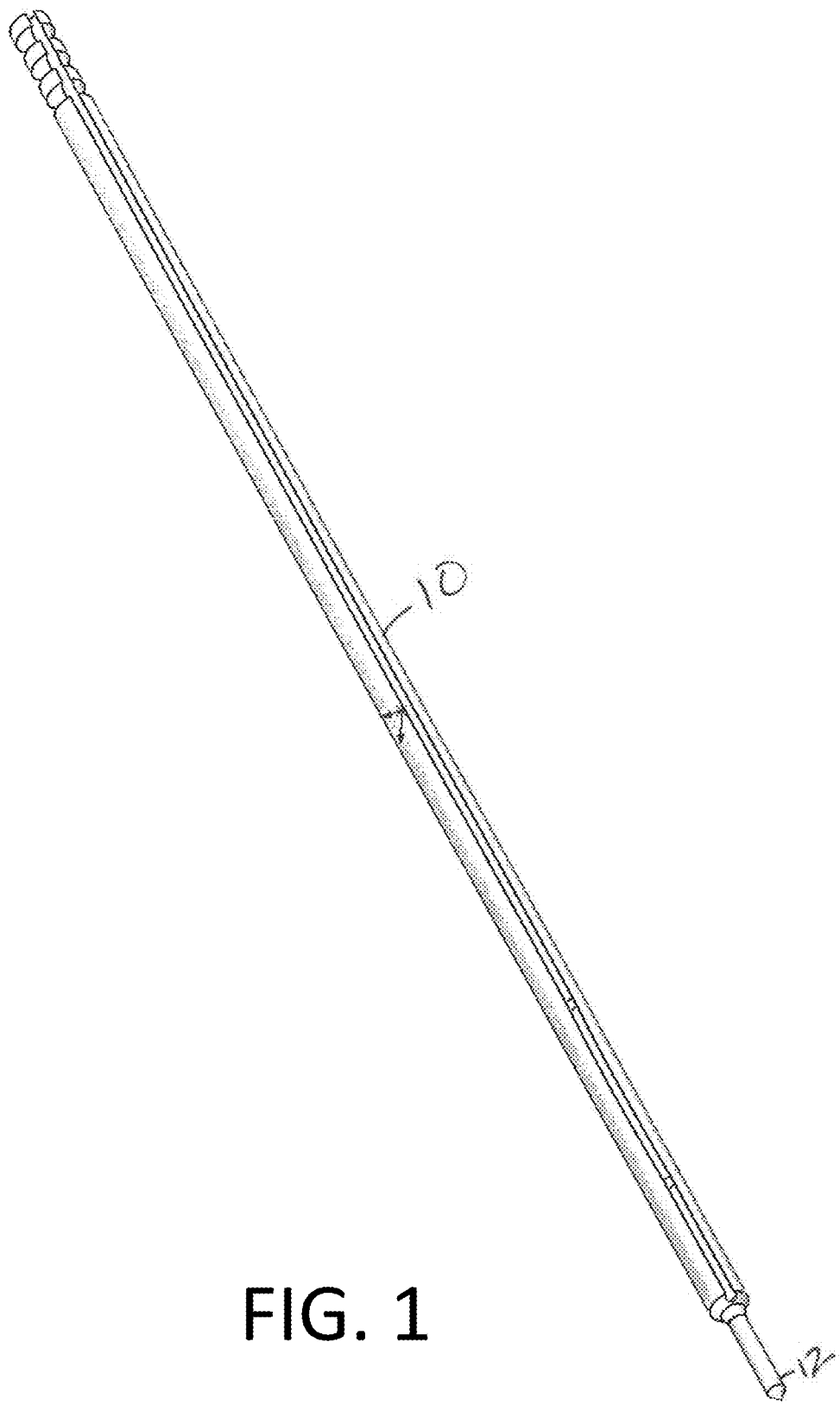
FIG. 1 is a perspective view of an ATP dilator in accordance with certain embodiments.

While the invention is amenable to various modifications and alternative forms, specifics thereof have been shown by way of example in the drawings and will be described in detail. It should be understood, however, that the intention is not to limit the invention to the particular example embodiments described. On the contrary, the invention is to cover all modifications, equivalents, and alternatives falling within the spirit and scope of the invention as defined by the appended claims.

DETAILED DESCRIPTION

In the following descriptions, the present invention will be explained with reference to example embodiments thereof, including a surgical method and tools used to perform the method. However, these embodiments are not intended to limit the present invention to any specific example, embodiment, environment, applications or particular implementations described in these embodiments. Therefore, description of these embodiments is only for purpose of illustration rather than to limit the present invention.

It should be appreciated that dimensional relationships among individual elements in the attached drawings are illustrated only for ease of understanding, but not to limit the actual scale.

A patient may be placed in a right lateral decubitus position (left side up). The patient may then be secured to the surgical table. Anterior-posterior (AP) imaging and lateral fluoroscopy may be used to confirm patient is positioned in a true lateral position.

Fluoroscopy may be used to confirm the target spinal motion segment. Initial reference markings may be placed at the $12^{th}$ rib, iliac crest, and target spinal level(s) with attention to the lordotic angles of the disc space(s). In one aspect a target trajectory may be established through the center of the disc space through the oblique corridor located between the ventral medial border of the psoas muscle and the left lateral border of the aorta (or iliac artery). This corridor may be widened primarily with retraction of the abdominal viscera.

Starting the incision ventral to the target disc space may allow passage of instruments on an oblique trajectory to the disc space that limits mobilization of the vessels and minimal, or no, dorsal retraction of the psoas muscle. As such, an incision may be started in the range of about 4-10 cm ventral to the center of the target spinal motion segment level. This entry point can be determined with CT scan during preoperative planning. The incision length may be determined by the number of target levels.

The incision may be made in an oblique plane, dorsal superior to ventral inferior, allowing easy separation of the external oblique muscle, with its fibers running in that same plane. However, due to the lack of bony restrictions in this flank area, the initial incision may be made in any plane.

Dissection may now be performed. Fibers of the lateral abdominal muscles (external oblique, internal oblique, and transverse abdominal) all run in different planes, therefore they should be split parallel to the fibers at each level. In an aspect, dissection proceeds carefully to avoid injury to the subcostal, iliohypogastric, and ilioinguinal nerves.

Accessing the L2-L3 motion segment, may require removal of the 12$^{th}$ rib. Approaching the L3-L4/L4-L5 spinal motion segment levels may be between the subcostal and iliohypogastric nerves. Approach to the L4-L5 spinal motion segment may be lower on the flank, which places the trajectory between the iliohypogastric and ilioinguinal nerves.

The surgical method does not require neuromonitoring. However instrumentation to do so is available, and can be used, if desired.

The dissection may continue by opening the medial fascial plane of the transversalis muscle. Finger dissection may then be directed in a dorsal medial direction down to the quadratus lumborum and the dorsal lateral psoas muscle. Dissection may continue ventrally along the lateral edge of the psoas muscle thus sweeping the peritoneal contents and ureter ventrally and past the ventral edge of the psoas muscle. The genitofemoral nerve most often emerges from the psoas muscle at the L2-3 level but it traverses inferiorly below the anterior fascia of the psoas. The nerve should be distinguished from the psoas minor muscle tendon that runs on the lateral aspect of the psoas and has a whiter, bundle-type appearance.

The sympathetic chain may be identified and then dissected from the spine and retracted ventrally. This will allow good visualization of the anterior longitudinal ligament, which should be preserved. Sharp dissection and cautery may be used to cut attachments of the psoas muscle from the spine if dorsal retraction of the muscle is necessary. Care should be taken to identify the segmental spinal arteries with abnormal trajectory near the endplates, which might enter the surgical field after retraction. These may need to be ligated to avoid significant intraoperative bleeding if damaged by the retraction.

Access to the intervertebral disc space may now be accomplished. After a safe retroperitoneal pathway to the anterior portion of the psoas has been established under direct visualization, an ATP dilator 10 (as shown in FIG. 1) may be advanced down to a disc space in front of the psoas muscle while using a finger and/or one or more handheld retractor(s) 20 (as shown in FIG. 2) to protect the peritoneal membrane and retract retroperitoneal fat.

Figure 2:
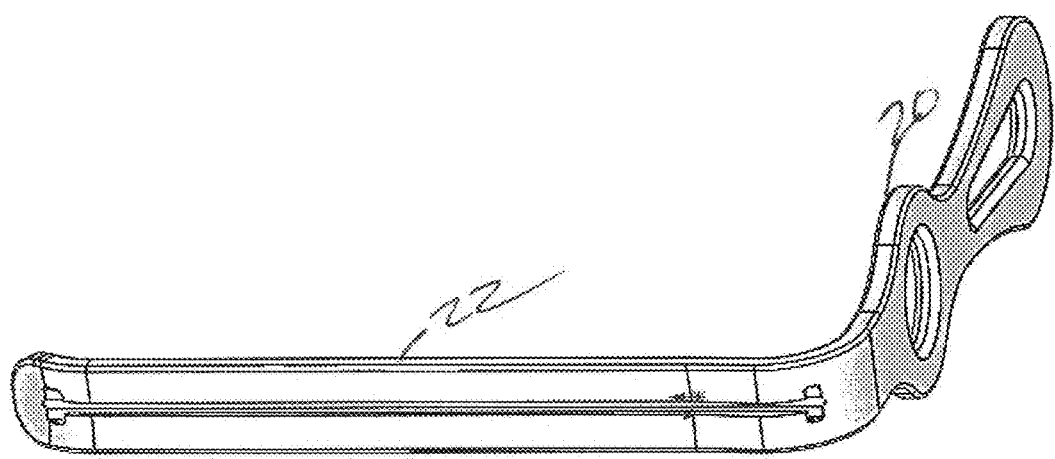
FIG. 2 is a perspective view of a retractor in accordance with certain embodiments.

Referring to FIG. 1, the ATP dilator 10 may include a pointed tip 12 to protrude into the disc space to secure the ATP dilator 10 in place during the surgical procedure. This also eliminating the need for a guidewire. In an alternative embodiment, a guide pin may be used instead of the ATP dilator 10. In a preferred embodiment, the ATP dilator 10 is a 5 mm dilator.

An ATP dilator 10 and ATP portal tube dilator 30 (shown in FIG. 3) may now be placed through the pathway to the disc space.

Figure 3:
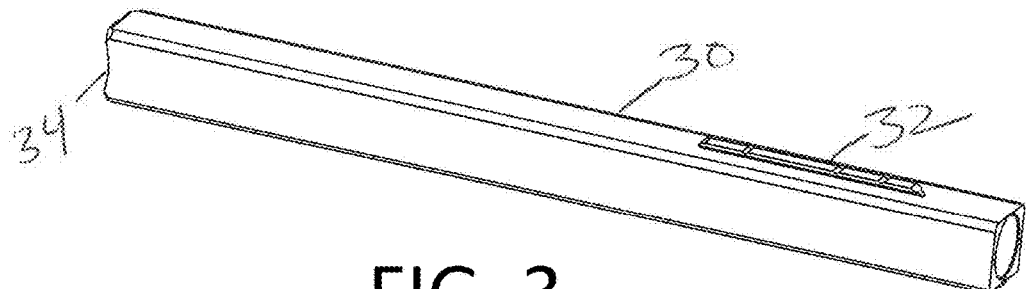
FIG. 3 is a perspective view of an ATP portal tube dilator in accordance with certain embodiments.
Figure 4:
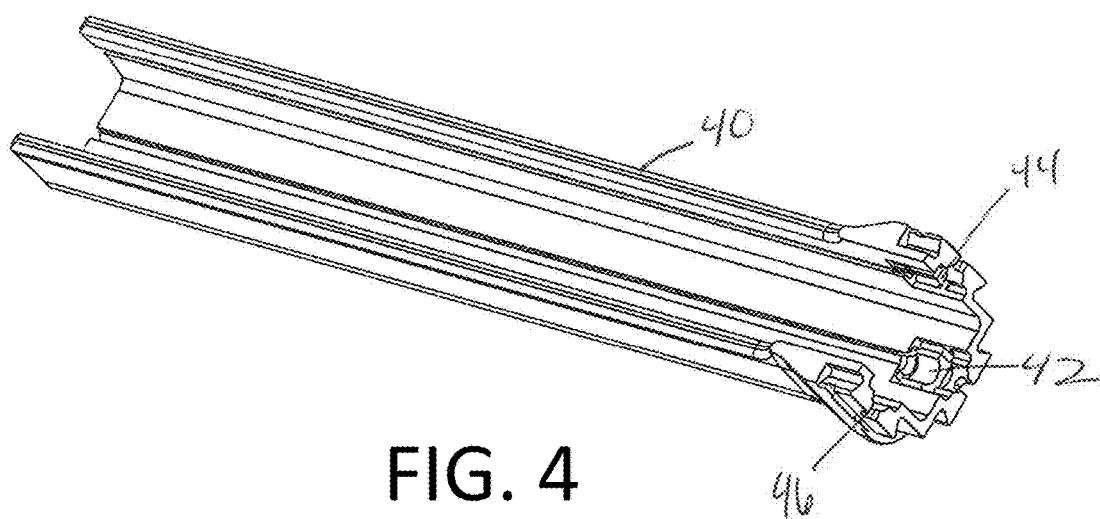
FIG. 4 is a perspective view of an ATP portal tube in accordance with certain embodiments.
Figure 5:
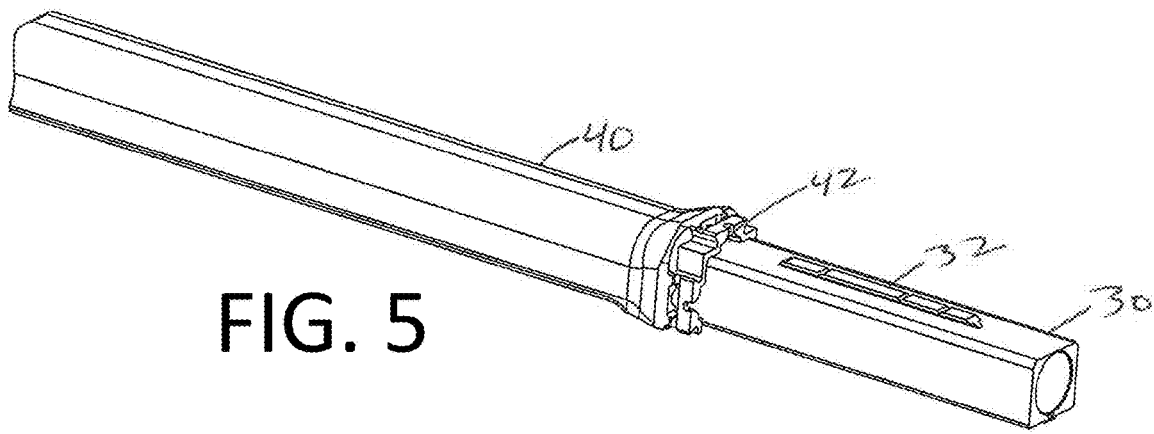
FIG. 5 is a perspective view of an ATP portal tube dilator engaged with an ATP portal tube in accordance with certain embodiments.
Figure 6:
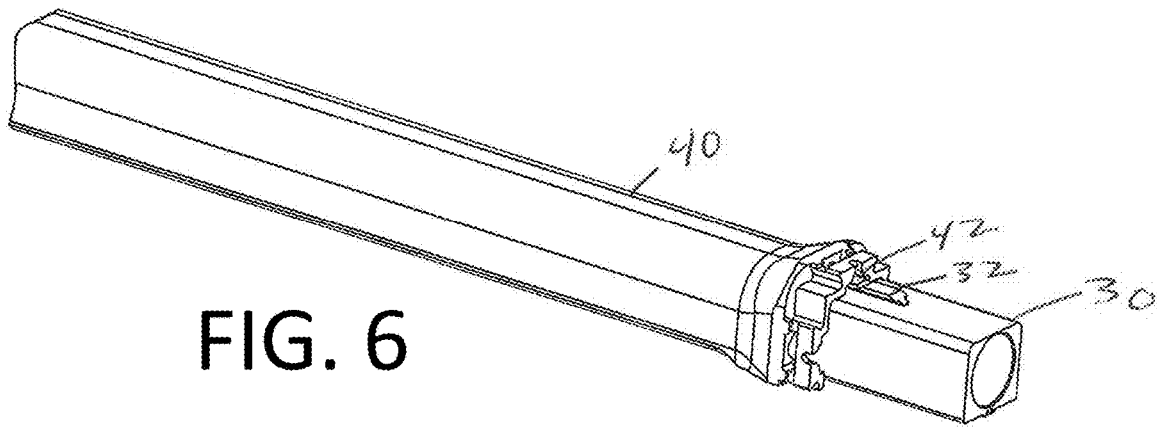
FIG. 6 is another perspective view of an ATP portal tube dilator engaged with an ATP portal tube in accordance with certain embodiments.
Figure 7:
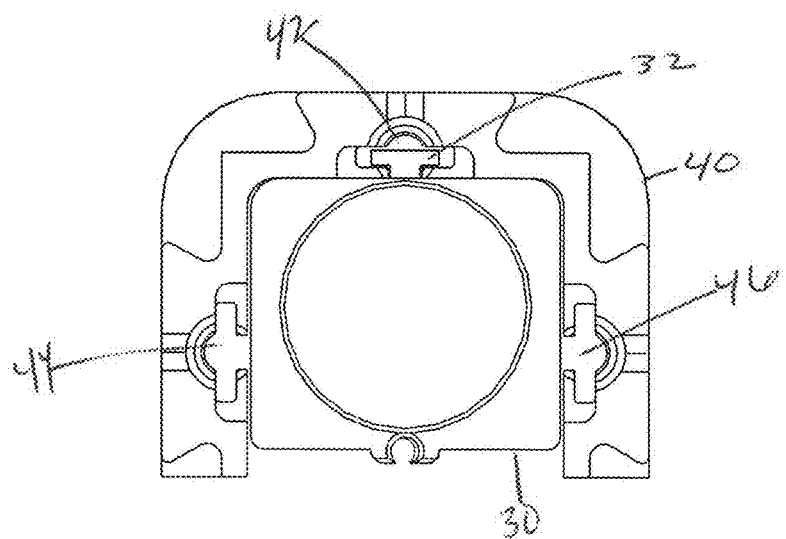
FIG. 7 is an end view of an ATP portal tube dilator engaged with an ATP portal tube in accordance with certain embodiments.
Figure 8:
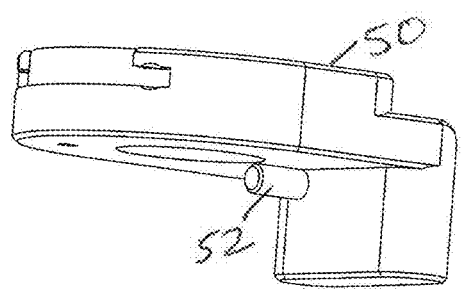
FIG. 8 is a perspective view of an ATP radial stop in accordance with certain embodiments.
Figure 9:
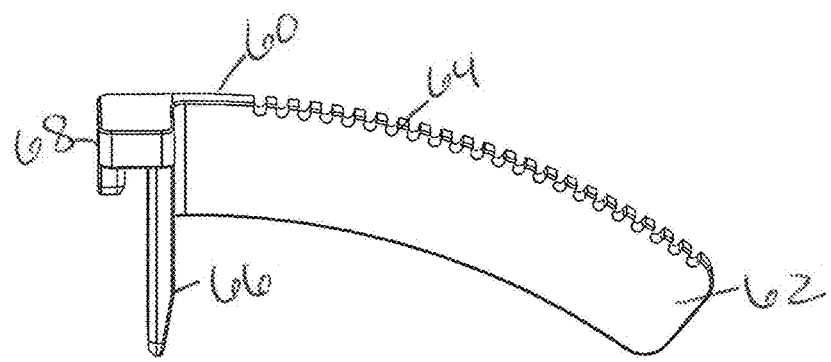
FIG. 9 is a perspective view of an ATP radial support in accordance with certain embodiments.

Referring to FIG. 3, the ATP portal tube dilator 30 may include an engagement feature 32 defined on an exterior surface thereof to engage with an ATP portal tube 40 (shown in FIG. 4). The ATP portal tube dilator 30 is sized and configured to fit within the inner channel defined in the ATP portal tube 40. The ATP portal tube dilator 30 may include a contoured proximal end 34 that is contoured to mimic a patient's anatomy.

In one embodiment, the ATP portal tube 40 may be a 3-walled portal as disclosed in US Patent Application Pub. No. US 2019/0091038 A1, entitled, Interbody Fusion System and Methods, the entirety of which is incorporated herein by reference.

Either a standard dilator or the ATP dilator 10 may be used to initiate access. The preferred starting position of the dilator on the disc space is ventral to the psoas and away from the major vessels. The position of the dilator's tip should be confirmed using lateral fluoroscopy. In a preferred embodiment, the entry point into the disc should be slightly ventral to the midpoint of the disc. Such an entry point may minimize the risk of injury to the contralateral foramen due to the oblique trajectory of disc preparation instruments and implant placement.

After the proper position of ATP dilator 10 has been established, the ATP dilator 10 may be advanced into the disc space. In an alternate embodiment where a standard dilator is used, a guide wire may be placed through the standard dilator and into the disc space.

Referring to now to FIGS. 3-7, the ATP portal tube dilator 30 may be positioned so that the engagement feature 32 that connects to the ATP portal tube 40 is positioned ventrally. The engagement feature 32 of the ATP portal tube dilator 30 may engage with a respectively-shaped channel or groove 42 defined in the inner channel of the ATP portal tube 40.

Handheld retractor(s) 20 may be radiolucent and may be placed to protect the vascular structures anteriorly.

The ATP portal tube 40 may then be advanced over the outer surface ATP portal tube dilator 30 with the open side of the ATP portal tube 40 facing posteriorly. The ATP portal tube 40 is advanced down to the disc space, ensuring the ventral channel 42 of ATP portal tube 40 engages the engagement feature 32 on the ATP portal tube dilator 30. The handheld retractor(s) 20 may then be removed.

The blade 22 of the hand-held retractor 20 may be sized and configured to fit inside the ATP portal tube 40, placed against the open-side of the ATP portal tube 40, effectively enclosing the ATP portal to create a 4-walled portal if preferred, without having to add an extra blade or toe-out a series of blades. In a preferred embodiment, the retractor blade 22 may be a 17×150 mm blade.

Next, a table arm/clamp assembly may be attached to the ATP portal tube 40. A 170 mm fixation pin may be placed in either the superior or inferior ATP portal tube 40 channel 44, 46 to secure the ATP portal tube 40 to the spine. Fixation Pins may be placed in both channels if desired. Placement of fixation pins(s) can be confirmed under fluoroscopy. The dilators and guide pin are then removed. Final position of the ATP portal tube 40 can be confirmed using lateral fluoroscopy.

A light cable may be placed down one of the ATP portal tube channels 42, 44, 46 and bent to achieve the desired illumination. In another embodiment, a light cable may be placed down a handheld retractor.

Shims may be used to minimize soft tissue creep and/or increase stability of the ATP portal tube 40 during the procedure. A shim may be inserted into channel(s) 42, 44, 46 of the ATP portal tube 40.

A discectomy may now be performed on the patient through the ATP portal tube 40. An annulotomy of about 18 mm in length may be made. More annulus may be undercut, beneath the psoas to facilitate rotation of instruments and implant into orthogonal position that is 90 degrees to the sagittal plane.

A thorough discectomy and endplate preparation may be performed using Cobb elevators, pituitary rongeurs, rakes, curettes, and/or other instruments, paying special attention to the endplate that is anterior and posterior to the ATP portal tube 40. The contralateral annulus may be released by rotating the Cobb(s) into an orthogonal positon 90 degrees to the sagittal plane.

Once satisfied with the discectomy, an implant may be selected. An implant trial may be used. In a preferred embodiment, implant trials may be sized with 0°, 8°, or 15° lordotic angles. Implant trials may be passed through the ATP Portal tube 40 obliquely and then turned/rotated to allow the surgeon to place them orthogonally across the disc space, perpendicular to the sagittal plane.

Implant trials may include four thru-holes located near the proximal end of the implant trial body. In a preferred embodiment, these thru-holes may indicate the location of the proximal edges of four Implant lengths, for example, but not limited to: 45 mm, 50 mm, 55 mm, and 60 mm. Once the distal end of the implant trial body is positioned, fluoroscopic imaging may be used to locate the thru-hole that aligns with the ipsilateral edge of the vertebral body and then the desired implant length may be determined. In an embodiment, the preferred implant length places the ends of the implant between the apophyses of the vertebral bodies. Trial position may be confirmed using lateral fluoroscopic imaging.

Figure 10:
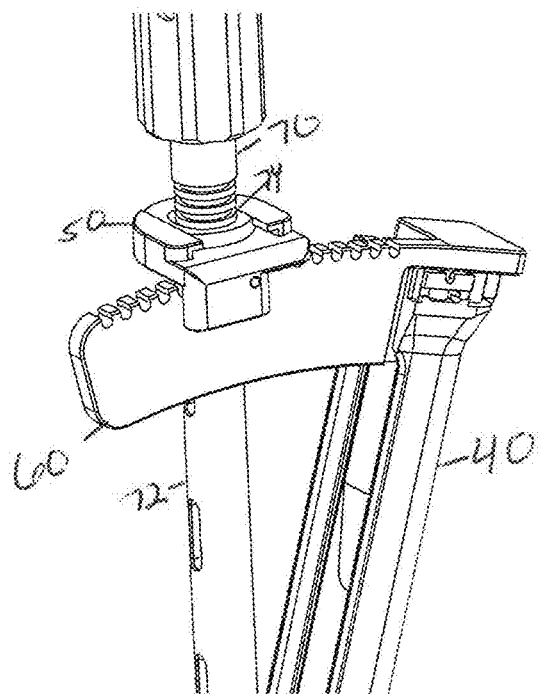
FIG. 10 is a perspective view of an implant inserter with an ATP radial stop engaged with an ATP radial support and portal tube in accordance with certain embodiments.
Figure 11:
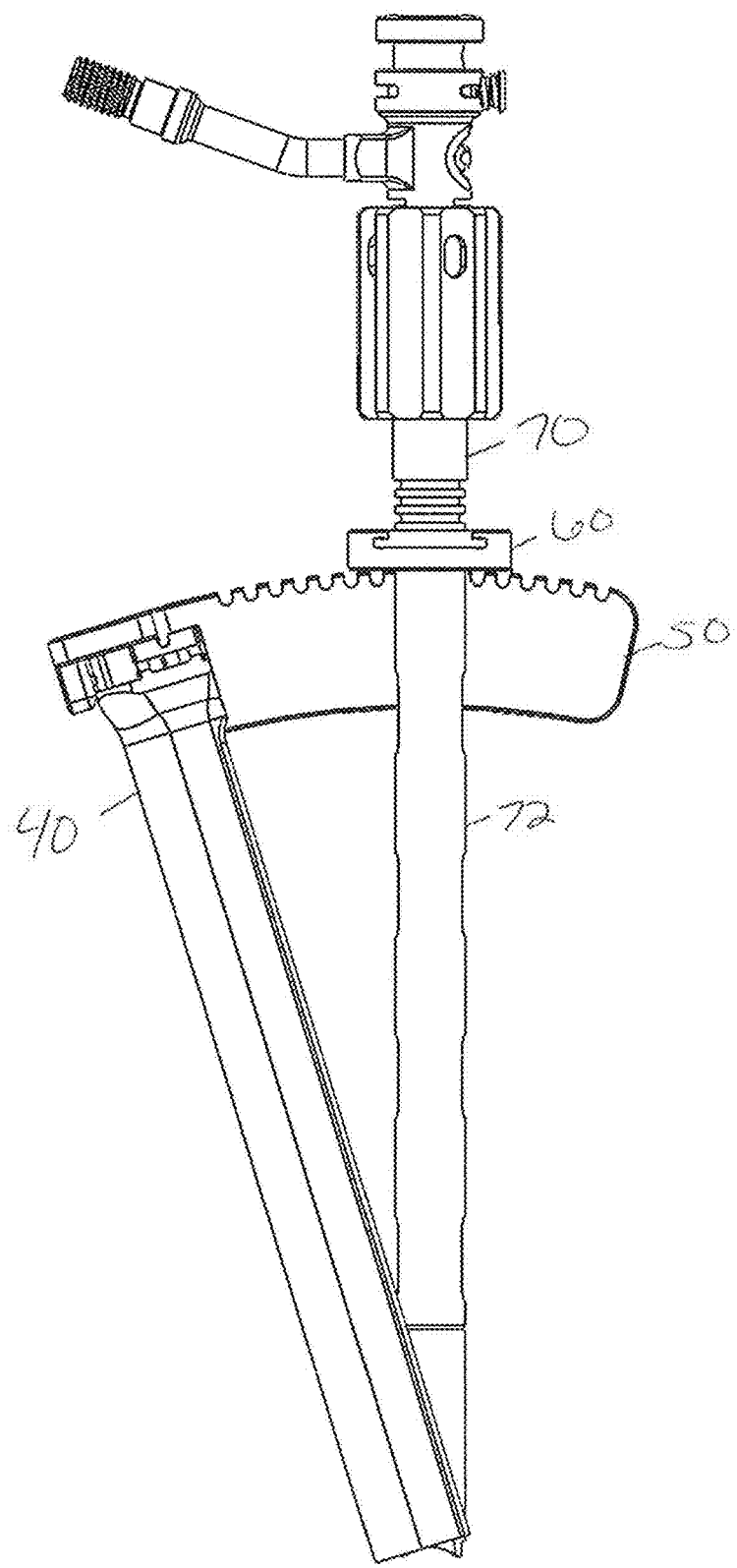
FIG. 11 is a side view of implant inserter with ATP radial stop engaged with an ATP radial support and portal tube in accordance with certain embodiments.

Referring to FIGS. 8-11, an ATP radial stop 50 may be loaded onto the shaft 72 of an inserter 70 (FIGS. 10-11). The ATP radial stop 50 may be positioned on the most distal grooves 74 of the inserter's shaft 72.

An implant may now be inserted into the disc space while monitoring placement under AP fluoroscopy. One suitable implant is disclosed in U.S. Pat. No. 10,111,756 B2, entitled, Mesh Spacer Hybrid, the entirety of which is incorporated herein by reference.

The inserter 70, having the implant loaded thereon, may enter the disc space obliquely and may be then turned/rotated orthogonally, 90 degrees to the sagittal plane, to allow placement of the implant across the disc space. Using the lateral image of the final trial position and direct visualization, the trajectory of the trial may be followed. In an alternate embodiment, if the imaging is not accurate, the trajectory may be altered as necessary to position the implant centrally from the anterior/posterior boarders of the disc space. The position of the implant may be confirmed using fluoroscopy.

In a preferred embodiment, complete rotation and alignment of the implant may be completed when approximately 50%-75% of an implant is inserted into the disc space. Lateral fluoroscopy and direct visualization may be used to help confirm implant distance into the disc space prior to turning/rotating inserter. The final positioning of an implant may be completed under AP fluoroscopy.

Referring again to FIGS. 8-11, an ATP radial support 60 may be attached to the ATP portal tube 40. The ATP radial support 60 may include an elongated arcuate arm 62. The arm 62 may include grooves, teeth or other engagement features 64 along its top edge. The ATP radial support 60 may further include a guide 66 sized and configured to fit down and engage with the ATP portal tube 40. The ATP radial support 60 may further include a forward stop 68 which fits into the top of the ATP portal tube 40 to prevent forward movement. The ATP radial support 60 provides a known stop and confirmation of implant placement under fluoroscopy.

The ATP radial stop 50 may be aligned on the shaft 72 of inserter 70 with the ATP radial support 60 to ensure that the implant is in the desired position. Male projecting feature 52 of the ATP radial stop 50 may be placed into one of the corresponding engagement features 64 of the ATP radial support 62.

The implant is confirmed to be positioned centrally in the disc space, from the anterior/posterior boarders of the disc space. ATP Radial support 60 and the ATP radial stop 50 allow for adjustments distal to the original initial stop location in known distance increments. Each groove 74 on the inserter 70, which is where the ATP radial stop 50 locks into the inserter 70, allows the implant to be advanced in controlled increments. For example, in a preferred example embodiment, the implant may be advanced in 3 mm increments further into the disc space. In such an example, the inserter 70 and ATP radial stop 50 combination allows the implant to be advanced a total of 9 mms in 3 mm increments.

The implant may be filled with autograft or allograft that is delivered through fill tubes.

Following placement of the implant, posterior fixation may be employed to complete the construct.

Any of the surgical tools or instruments described herein can be provided together as part of a kit. The kit may include one or more implants. The kit may also include a surgical guide and/or instructions for use of the surgical tools and/or the implant.

Any two or more tools described herein can be collectively referred to as a system. The system may also include one or more implants, a surgical guide and/or instructions for use of the surgical tools and/or the implant.

The present invention may be embodied in other specific forms without departing from the spirit or essential attributes thereof, and it is, therefore, desired that the present embodiment be considered in all respects as illustrative and not restrictive. Those skilled in the art may recognize other equivalents to the specific embodiment described herein which equivalents are intended to be encompassed by the claims attached hereto.

What is claimed is:

1. A method of performing a spinal fusion surgical procedure via an Anterior to the Psoas (ATP) approach, the method comprising:
   forming a surgical pathway in a patient's tissues to access a disc space through an oblique corridor located between a ventral medial border of a psoas muscle and a left lateral border of an aorta or iliac artery.

2. The method of claim 1, further comprising performing a discectomy through the surgical pathway.

3. The method of claim 1, further comprising placing an intervertebral implant within the disc space through the surgical pathway.

4. The method of claim 1, further comprising, advancing a portal tube through the surgical pathway down to the disc space.

* * * * *